(12) United States Patent
Yoshida et al.

(10) Patent No.: US 8,901,254 B2
(45) Date of Patent: Dec. 2, 2014

(54) PROCESS FOR PREPARING POLYCARBONATE DIOL DIACRYLATE AND HIGH-PURITY POLYCARBONATE DIOL DIACRYLATE

(75) Inventors: Youichi Yoshida, Ube (JP); Yasuhito Yamamoto, Ube (JP); Kenji Hirotsu, Ube (JP)

(73) Assignee: Ube Industries, Ltd., Ube-Shi (JP)

( * ) Notice: Subject to any disclaimer, the term of this patent is extended or adjusted under 35 U.S.C. 154(b) by 242 days.

(21) Appl. No.: 13/638,550

(22) PCT Filed: Mar. 28, 2011

(86) PCT No.: PCT/JP2011/057533
§ 371 (c)(1),
(2), (4) Date: Sep. 28, 2012

(87) PCT Pub. No.: WO2011/122520
PCT Pub. Date: Oct. 6, 2011

(65) Prior Publication Data
US 2013/0023630 A1    Jan. 24, 2013

(30) Foreign Application Priority Data

Mar. 29, 2010 (JP) .................................. 2010-075884
Dec. 6, 2010 (JP) .................................. 2010-271918

(51) Int. Cl.
| | | |
|---|---|---|
| C08F 283/00 | (2006.01) | |
| C08G 64/04 | (2006.01) | |
| C12P 7/62 | (2006.01) | |
| C08G 64/02 | (2006.01) | |
| C08G 64/42 | (2006.01) | |
| C08F 283/02 | (2006.01) | |

(52) U.S. Cl.
CPC .............. *C08G 64/42* (2013.01); *C08G 64/045* (2013.01); *C12P 7/62* (2013.01); *C08G 64/0291* (2013.01)
USPC .......................................... 525/461; 435/135

(58) Field of Classification Search
USPC .......................................... 525/461; 435/135
See application file for complete search history.

(56) References Cited

U.S. PATENT DOCUMENTS

| 5,444,104 A | 8/1995 | Waknine |
|---|---|---|
| 2002/0018938 A1 | 2/2002 | Takeuchi et al. |

FOREIGN PATENT DOCUMENTS

| EP | 0 092 269 A1 | 10/1983 |
|---|---|---|
| EP | 2 253 710 A1 | 11/2010 |
| JP | 2001-15730 A | 6/2001 |
| JP | 2002-25335 A | 1/2002 |
| JP | 2004-275064 A | 10/2004 |
| JP | 2009-157125 A | 7/2009 |
| JP | 2009-291167 A | 12/2009 |
| WO | WO 2009/042825 A2 | 4/2009 |
| WO | 2009/102069 A1 | 8/2009 |

OTHER PUBLICATIONS

Athawale et al., "Enzymatic synthesis of the acrylic esters: a comparative study", Journal of Molecular Catalysis B: Enzymatic 10, 2000, pp. 551-554.
International Search Report for PCT/JP2011/057533 dated Apr. 19, 2011.
Nordblad at al., "Enzymatic synthesis of polymer acrylates and their evaluation as wood coatings", Industrial Biotechnology, vol. 5, No. 2, Summer 2009, pp. 110-118.
International Preliminary Report on Patentability for corresponding International Patent Application No. PCT/JP2011/057533, dated Nov. 1, 2012.
Extended European Search Report, dated Sep. 13, 2013, for European Application No. 11762744.8.
Puskas et al., "Green Polymer Chemistry Using Nature's Catalysts, Enzymes", Journal of Polymer Science: Part A: Polymer Chemistry, vol. 47, XP-002638405, 2009, pp. 2959-2976.
European Official Communication for European Application No. 11762744.8, dated Apr. 14, 2014.
Itoh et al., "Lipase-Catalyzed Enantioselective Acylation in the Ionic Liquid Solvent System: Reaction of Enzyme Anchored to the Solvent," Chemistry Letters, No. 3, Jan. 1, 2001, XP055113089, pp. 262-263.

*Primary Examiner* — Terressa Boykin
(74) *Attorney, Agent, or Firm* — Birch, Stewart, Kolasch & Birch, LLP

(57) ABSTRACT

This is to provide a process for preparing a polycarbonate diol diacrylate from a polycarbonate diol and a vinyl acrylate compound without using a protonic acid or a metal component.

This is a process for preparing a polycarbonate diol diacrylate which comprises reacting a polycarbonate diol represented by the formula (I) and a vinyl acrylate compound represented by the formula (II) in the presence of a hydrolase, and a polycarbonate diol diacrylate represented by the formula (III) having a terminal acrylated ratio of 97% or more.

11 Claims, No Drawings

PROCESS FOR PREPARING POLYCARBONATE DIOL DIACRYLATE AND HIGH-PURITY POLYCARBONATE DIOL DIACRYLATE

TECHNICAL FIELD

The present invention relates to a process for preparing a polycarbonate diol diacrylate. The present invention also relates to a high-purity polycarbonate diol diacrylate.

BACKGROUND ART

The polycarbonate diol diacrylate is a compound useful as a starting material for ink, a paint, a coating material, an adhesive, a photocurable resin, a cross-linking agent, an electrolyte material, and other resins, etc. For example, in Patent Literature 1, there is disclosed an optical waveguide in the form of a film using a polycarbonate diol diacrylate.

As a method for preparing a polycarbonate diol diacrylate, it has been known a method wherein a polycarbonate diol and an acrylic acid are reacted in the presence of a protonic acid catalyst such as p-toluenesulfonic acid, etc. (for example, see Patent Literature 2).

However, according to this method, there is a serious problem that the resulting polycarbonate diol diacrylate is colored to brown color which is concerned with the quality of the product. Moreover, according to this method, acrylic acid as a starting material is used excessively, so that even when it is removed by neutralization and washing after the synthesis, an acid catalyst, a sulfur component caused by the starting material, or impurities remain in the resulting product, whereby there is a problem that worsening of the quality of the product (bad smell, metal corrosion) is likely caused.

It has been also known a process for preparing a polycarbonate diol diacrylate wherein a polycarbonate diol and an acrylic acid ester compound are reacted in the presence of an organometallic catalyst while removing a forming alcohol (for example, see Patent Literature 3). However, according to this method, the forming alcohol may exchange to the carbonate bond in the polycarbonate diol to form an alkoxy terminal. The alkoxy terminal lowers the cross-linking density of the cured product in the later curing step, so that the formation thereof shall be desirably avoided. In addition, residue of the metal component derived from the organometallic catalyst can affect the quality of the product, so that decomposition and recovering steps of the catalyst component are required. Moreover, according to this method, when the by-produced alcohol is distilled off, there is a problem that the starting acrylic acid ester is azeotroped with the alcohol and distilled out from the reaction system. In addition, there is a problem that a popcorn polymerization due to vaporized starting acrylic acid ester may be caused.

Here, the popcorn polymerization is a phenomenon that forms a polymer which becomes a core mainly in a vapor phase, and causes polymerization explosively from the polymer as a starting point accompanying with a high temperature heat of polymerization, and forms a porous bulky polymerized product. If the popcorn polymerization occurred during a large scale preparation process, there is a fear that it may cause clogging of the apparatus which leads breakage of the facilities and explosion of the same, so that a preparation process which can prevent from increase in a vinyl compound concentration and can carry out at a low temperature has been desired.

It has been known as a method for acrylating the free hydroxyl group at a relatively lower temperature without using an acid catalyst or a metal component, a method of using a lipase as an enzymatic catalyst (for example, see Non-Patent Literature 1). Also, it has been reported that it is possible to produce an acrylic acid ester in a non-polar solvent by using vinyl acrylate and an immobilized lipase (for example, see Non-Patent Literature 2). However, it has never been known an example in which acrylation is carried out by using a polycarbonate diol as a substrate and a lipase.

PRIOR ART LITERATURES

Patent Literatures

[Patent Literature 1] JP 2009-157125A
[Patent Literature 2] JP 2002-25335A
[Patent Literature 3] JP 2001-151730A

Non-Patent Literature

[Non-Patent Literature 1] Industrial Biotechnology, vol. 5, page 110 (2009)
[Non-Patent Literature 2] Journal of Molecular Catalysis B: Enzymatic vol. 10, page 551 (2000)

DISCLOSURE OF THE INVENTION

Problems to be Solved by the Invention

An object of the present invention is to solve the above-mentioned problems in the prior art. More specifically, this is to provide a process for preparing a polycarbonate diol diacrylate from a polycarbonate diol and a vinyl acrylate compound without using a protonic acid or a metal component. Here, the polycarbonate diol diacrylate is referred to a compound in which the terminal hydroxyl group of the polycarbonate diol is acrylated by an acrylic acid ester compound. Also, an object of the present invention is to provide a high-purity polycarbonate diol diacrylate.

Means to Solve the Problems

The present inventors have earnestly studied to solve the above-mentioned problems, and as a result, they have found out a novel industrial preparation process comprising subjecting a polycarbonate diol and a vinyl acrylate compound to transesterification in the presence of a hydrolase (in particular, a lipase) to prepare a polycarbonate diol diacrylate, whereby accomplished the present invention.

The present invention relates to a process for preparing a polycarbonate diol diacrylate which comprises reacting a polycarbonate diol represented by the formula (I):

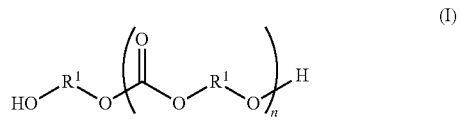

wherein
$R^1$ is the same or different, each represents a divalent group comprising one or more linear, branched or cyclic alkylene group, the divalent group may have a substituent(s), and/or one or more non-terminal carbon atoms may be replaced by a divalent aromatic group, a divalent heterocyclic group, an oxygen atom or a sulfur atom, or represents a divalent cross-linked carbon ring group, and n represents an average polymerization degree, and a number of 1 to 50, with a vinyl acrylate compound represented by the formula (II):

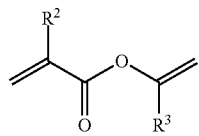

wherein
$R^2$ represents a hydrogen atom or a linear or branched alkyl group having 1 to 4 carbon atoms, and
$R^3$ represents a hydrogen atom or a linear, branched or cyclic alkyl group having 1 to 10 carbon atoms, in the presence of a hydrolase.

The present invention relates to the above-mentioned process for preparing a polycarbonate diol diacrylate, wherein the hydrolase is a lipase.

The present invention relates to the above-mentioned process for preparing a polycarbonate diol diacrylate, wherein the lipase is an immobilized lipase.

The present invention relates to the above-mentioned process for preparing a polycarbonate diol diacrylate, wherein the reaction is carried out in a flow tube reactor filled with an immobilized lipase.

Also, the present invention relates to the above-mentioned process for preparing a polycarbonate diol diacrylate, wherein the lipase is a lipase originated from *Candida antarctica*.

The present invention relates to a polycarbonate diol diacrylate represented by the formula (III):

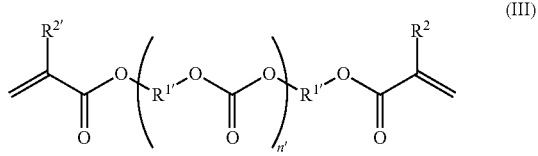

wherein
$R^{1'}$ is the same or different, each represents a divalent group comprising one or more linear, branched or cyclic alkylene group, the divalent group may have a substituent(s), and/or one or more non-terminal carbon atoms may be replaced by a divalent aromatic group, a divalent heterocyclic group, an oxygen atom or a sulfur atom, or a divalent cross-linked carbon ring group,
$R^{2'}$ represents a hydrogen atom or a linear or branched alkyl group having 1 to 4 carbon atoms,
n' represents an average polymerization degree, and a number of 1 to 50, having a terminal acrylated ratio of 97% or more.

Effects of the Invention

According to the process of the present invention, a polycarbonate diol diacrylate can be prepared from a polycarbonate diol and a vinyl acrylate compound using a hydrolase as a catalyst without using a protonic acid or a metal component. According to the process of the present invention, the reaction can be carried out at a lower temperature as compared with the case where transesterification is carried out while refluxing the acrylic acid ester at normal pressure, so that it is excellent in the points of efficiency and safety. Incidentally, by using a compound having a molecular structure of the vinyl acrylate ester in the reaction with a polycarbonate diol, vinyl alcohol is formed as a by-product. This compound immediately isomerizes to a carbonyl compound which is a keto form, so that it can be considered to have an effect of shifting the equilibrium of said reaction to the generators. Also, there is also an effect that the side reaction such as an exchange reaction of an alcohol which is a by-product and the main chain carbonate, etc., can be inhibited.

Also, according to the present invention, a high-purity polycarbonate diol diacrylate having a terminal acrylated ratio of 97% or more can be provided. Such a polycarbonate diol diacrylate is suitable for a coating material, an adhesive, etc., since a cross-linked density is not lowered when it is cured.

BEST MODE TO CARRY OUT THE INVENTION

In the process of the present invention, a polycarbonate diol diacrylate can be obtained by reacting a polycarbonate diol with a vinyl acrylate compound in the presence of a hydrolase.

(Polycarbonate Diol)
The polycarbonate diol to be used in the present invention is represented by the formula (I):

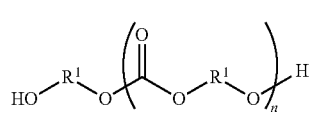

wherein
$R^1$ is the same or different, each represents a divalent group comprising one or more linear, branched or cyclic alkylene group, the divalent group may have a substituent(s), and/or one or more non-terminal carbon atoms may be replaced by a divalent aromatic group, a divalent heterocyclic group, an oxygen atom or a sulfur atom, or represents a divalent cross-linked carbon ring group, and
n represents an average polymerization degree, and a number of 1 to 50.

The divalent group comprising one or more linear, branched or cyclic alkylene group may be mentioned, for example, a divalent group comprising a linear or branched alkylene group-cyclic alkylene group, a divalent group comprising a linear or branched alkylene group-cyclic alkylene group-linear or branched alkylene group, and a divalent group comprising a cyclic alkylene group-linear or branched alkylene group-cyclic alkylene group.

A carbon number of the linear or branched alkylene group is preferably 1 to 25, more preferably 3 to 12, for example, a propylene group, a butylene group, a pentylene group, a hexylene group, a 3-methylpentylene group, a heptylene group, an octylene group, a decylene group, etc., preferably a butylene group, a pentylene group, a hexylene group and a 3-methylpentylene group.

A carbon number of the cyclic alkylene group is preferably 3 to 25, more preferably 3 to 12. The cyclic alkylene group is preferably a cycloalkylene having 3 to 12 carbon atoms, and there may be mentioned, for example, a cyclopropylene group, a cyclobutylene group, a cyclopentylene group, a cyclohexylene group, a cycloheptylene group, a cyclooctylene group, etc., preferably a cyclohexylene group.

The divalent group comprising the above-mentioned linear or branched alkylene group-cyclic alkylene group-linear or branched alkylene group may be mentioned, for example, a cyclopentane-1,3-dimethylene group, a cyclohexane-1,4-dimethylene group, etc., preferably a cyclohexane-1,4-dimethylene group.

The above-mentioned divalent group may have a substituent(s) (for example, a benzene-1,4-dimethylene group), and/or one or more carbon atoms other than the terminals of the divalent group (when the divalent group has a substituent(s), the portion other than the substituent(s)) may be replaced by a divalent aromatic group (for example, a phenylene group, a naphthylene group), a divalent heterocyclic group (for example, a pyridanyl group), an oxygen atom or a sulfur atom.

The substituent(s) may be mentioned a linear or branched alkyl group having 1 to 6 carbon atoms (for example, a methyl group, an ethyl group), a cycloalkyl group having 3 to 12 carbon atoms (for example, a cyclohexyl group), an aralkyl group having 7 to 10 carbon atoms (for example, a benzyl group), an aryl group having 6 to 12 carbon atoms (for example, a phenyl group, a tolyl group), an alkoxy group having 1 to 6 carbon atoms (for example, a methoxy group, an ethoxy group) and a halogen atom (for example, a fluorine atom, a chlorine atom).

$R^1$ may be a divalent group of a cross-linked carbon ring. Here, "the cross-linked carbon ring" means a carbon ring in which two carbon atoms which are not adjacent to each other are cross-linked by a cross-linking group or a direct bond. The divalent group of the cross-linked carbon ring is preferably a divalent group of a cross-linked carbon ring having 6 to 10 carbon atoms, and there may be mentioned, for example, bicyclo-[2.1.1]-hexane-diyl, bicyclo-[2.2.1]-heptane-diyl, bicyclo-[2.2.2]-octane-diyl, bicyclo-[3.3.0]-octane-diyl, bicyclo-[4.3.0]-nonane-diyl, bicyclo-[4.4.0]-decane-diyl and adamantane-diyl.

$R^1$ is preferably one or more selected from a propylene group, a butylene group, a pentylene group, a hexylene group, a 3-methylpentylene group, a cyclohexane-1,4-dimethylene group and a benzene-1,4-dimethylene group.

In the formula (I), n represents an average polymerization degree, and a number of 1 to 50, preferably 2 to 25. The average polymerization degree can be measured by an end-group determination using $^1$H-NMR.

The polycarbonate diol of the formula (I) may be any material prepared by any methods. For example, there may be used a polycarbonate diol prepared by transesterification of a divalent alcohol (HO—$R^1$—OH) having a group corresponding to $R^1$ of the formula (I) and a carbonic acid ester (for example, dimethyl carbonate, diethyl carbonate, dibutyl carbonate, diphenyl carbonate), or a polycarbonate diol prepared by the reaction of the above-mentioned divalent alcohol and chloroformate or phosgene. The divalent alcohol may be mentioned, for example, an aliphatic divalent alcohol having an alkylene group which has 4 to 25 carbon atoms (preferably 4 to 15 carbon atoms). Or else, a polycarbonate diol prepared by ring-opening polymerization of a cyclic carbonic acid ester, etc., can be also used. The cyclic carbonic acid ester may be mentioned, for example, a cyclic carbonic acid ester having an alkylene group which has 2 to 25 carbon atoms (preferably 2 to 15 carbon atoms).

Of these, a polycarbonate diol prepared by transesterification of an aliphatic divalent alcohol having an alkylene group which has 4 to 25 carbon atoms (preferably having 4 to 15 carbon atoms) and a carbonic acid ester is preferred. Such an aliphatic divalent alcohol may be mentioned a divalent alcohol wherein $R^1$ corresponds to a linear or branched alkylene group having 4 to 15 carbon atoms, and more specifically mentioned those having a trimethylene portion such as 2-methyl-1,3-propanediol, 1,3-butanediol, 2,4-heptanediol, 2,2-diethyl-1,3-propanediol, 2-methyl-2-propyl-1,3-propanediol, 2-ethyl-1,3-hexanediol, 2-methyl-2,4-pentanediol, 2,2,4-trimethyl-1,3-pentanediol, 2-butyl-2-ethyl-1,3-propanediol, etc., those having a tetramethylene portion such as 1,4-butanediol, etc., those having a pentamethylene portion such as 1,5-pentanediol, 3-methyl-1,5-pentanediol, 2,2-diethyl-1,5-pentanediol, 1,5-hexanediol, etc., those having a hexamethylene portion such as 1,6-hexanediol, 2-ethyl-1,6-hexanediol, etc., those having a heptamethylene portion such as 1,7-heptanediol, etc., those having an octamethylene portion such as 1,8-octanediol and 2-methyl-1,8-octanediol, 1,9-nonanediol, 1,10-decanediol, 1,11-undecanediol, 1,12-dodecanediol and 1,20-eicosanediol. Also, there may be mentioned a divalent alcohol wherein $R^1$ corresponds to a cycloalkylene group having 4 to 15 carbon atoms, and more specifically mentioned 1,3-cyclohexanediol, 1,4-cyclohexanediol, cyclohexane-1,4-dimethanol and cyclohexane-1,4-diethanol. In addition, 2,2-bis(4-hydroxycyclohexyl)propane, etc., which is a divalent alcohol wherein $R^1$ corresponds to a cycloalkylene-linear or branched alkylene-cycloalkylene can be used.

However, a divalent alcohol other than the above may be used, and there may be mentioned, for example, those in which $R^1$ is an alkylene group replaced by an oxygen atom such as diethylene glycol, triethylene glycol, polyethylene glycol, dipropylene glycol, polypropylene glycol and polytetramethylene glycol, those in which $R^1$ is a linear or branched alkylene-cycloalkylene-linear or branched alkylene group replaced by an oxygen atom such as 1,4-bis(hydroxyethoxy)cyclohexane, and those in which $R^1$ is a cycloalkylene-linear or branched alkylene group replaced by a linear or branched alkylene-oxygen atom such as 2,5-tetrahydrofurandimethanol. In addition, 2,7-norbornane diol which is a divalent alcohol of a cross-linked carbon ring may be also used.

Further, those in which $R^1$ is an alkylene group replaced by a divalent aromatic group which is unsubstituted or substituted by a halogen atom(s) such as p-xylylenediol, p-tetrachloroxylylenediol, benzene-1,4-dimethanol, etc., may be used. Moreover, those in which $R^1$ is an alkylene group replaced by one or more oxygen atoms and one or more divalent aromatic group such as 1,4-bis(hydroxyethoxy)benzene, 2,2-bis[(4-hydroxyethoxy)phenyl]propane, etc., may be used. The divalent alcohol in which $R^1$ has a divalent aromatic group is preferably 25% by mass or less based on the whole divalent alcohol, preferably 20% by mass or less, further preferably 15% by mass or less.

In the polycarbonate diol to be used in the present invention, $R^1$ may be the same or different from each other. That is, when the polycarbonate diol is to be obtained by transesterification of a divalent alcohol and a carbonic acid ester, or by the reaction of a divalent alcohol and chloroformate or phosgene, the divalent alcohol may be used alone, or two or more in combination. Also, when the polycarbonate diol is obtained by ring-opening polymerization of the cyclic carbonic acid ester, the cyclic carbonic acid ester may be used alone, or two or more in combination.

The polycarbonate diol of the formula (I) is preferably a polycarbonate diol in which $R^1$ is one or more selected from a propylene group, a butylene group, a pentylene group, a hexylene group, a 3-methylpentylene group, a cyclohexane-1,4-dimethylene group and a benzene-1,4-dimethylene group in the point of easily handling. The polycarbonate diol of the formula (I) may be used alone, or two or more in combination.

(Vinyl Acrylate Compound)

The vinyl acrylate compound to be used in the present invention is represented by the formula (II):

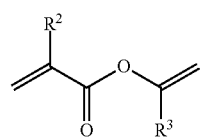

(II)

wherein $R^2$ represents a hydrogen atom or a linear or branched alkyl group having 1 to 4 carbon atoms, $R^3$ represents a hydrogen atom or a linear, branched or cyclic alkyl group having 1 to 10 carbon atoms.

When $R^2$ is a linear or branched alkyl group having 1 to 4 carbon atoms, there may be mentioned, for example, a methyl group and an ethyl group. When $R^3$ is a linear, branched or cyclic alkyl group having 1 to 10 carbon atoms, there may be mentioned, for example, a methyl group, an ethyl group, a propyl group, a butyl group, a pentyl group, a hexyl group, an octyl group, a decyl group, a cyclopentyl group and a cyclohexyl group.

$R^2$ is preferably a hydrogen atom or a methyl group. $R^3$ is preferably a hydrogen atom, a methyl group or an ethyl group.

The vinyl acrylate compound of the formula (II) may be mentioned an acrylic acid alkenyl ester such as vinyl acrylate, isopropenyl acrylate, etc., a methacrylic acid alkenyl ester such as vinyl methacrylate, isopropenyl methacrylate, etc. Of these, vinyl acrylate and vinyl methacrylate are preferred.

The vinyl acrylate compound of the formula (II) may be used alone, or two or more in combination.

An amount of the vinyl acrylate compound can be 0.5 to 60 mol based on 1 mol of the polycarbonate diol, and preferably 0.5 to 20 mol. The molar number of the polycarbonate diol can be calculated from an average molecular weight obtained by $^1$H-NMR (terminal hydroxyl value) (for example, see "Koubunshi Jikkengaku" vol. 18 (Magnetic resonance of polymer) p. 283, Kyoritsu Shuppan (published in 1975)).

(Scope of Hydrolase)

The hydrolase to be used in the present invention may be mentioned, for example, a protease, an esterase and a lipase, preferably a porcine liver esterase (PLE), a porcine pancreatic lipase (PPL), a cutinase or a lipase of a microorganism which can be isolated from yeast or bacteria, more preferably a cutinase originated from *Cryptococcus* sp, a lipase originated from *Burkholderia cepacia* (for example, Amano PS (available from Amano Enzyme Co.)), a lipase originated from *Candida antarctica* (for example, Novozym 435 (available from Novozymes)), a lipase originated from *Rhizomucor Miehei* (for example, Lipozyme RM IM (available from Novozymes)), a lipase originated from *Thermomyces lanuginosus* (Lipase TL), a lipase originated from *Mucor Miehei* (Lipase MM), particularly preferably a lipase originated from *Candida antarctica*.

These hydrolases may be a material in which a gene encoding the hydrolase obtained from the above-mentioned microorganisms is introduced into a suitable host such as yeast and a filamentous fungus, and the obtained recombinant is cultured.

The recombinant DNA technique to be used for expressing recombination of the hydrolase is well known in this field of the art. The amino acid sequence of the hydrolase is not limited only by the above-mentioned one, and there may be used, for example, a protein comprising an amino acid sequence in which one or several amino acids is/are deleted, substituted or added in these sequences, and having a hydrolysis activity can be suitably used in the present invention. Or else, a protein comprising an amino acid sequence showing, for example, 90% or more, preferably 95% or more, and more preferably 97% or more of sequence identity to these sequences, and having a hydrolysis activity can be also suitably used in the present invention.

The form of these hydrolases is not particularly limited, and may be in the form of a natural or immobilized enzyme.

The immobilized enzyme means a material in which a hydrolase is carried on an immobilizing carrier by adsorption, etc. The immobilizing carrier may be mentioned inorganic carriers such as Celite, diatomaceous earth, kaolinite, silica gel, molecular sieves, porous glass, activated carbon, calcium carbonate and ceramics, ceramics powder, organic polymers such as polyvinyl alcohol, polypropylene, chitosan, an ion-exchange resin, a hydrophobic absorbent resin, a chelating resin, a synthetic adsorptive resin, etc., and a hydrophobic absorbent resin is particularly preferred since it has a high adsorptive power of an enzyme. Among the hydrophobic absorbent resins, a porous resin is preferred since it can heighten an adsorbed amount of the enzyme due to its large surface area.

The hydrolase may be used alone, or two or more in combination.

An amount of the hydrolase is preferably 0.1 to 1000 mg, more preferably 1 to 200 mg, particularly preferably 1 to 10 mg based on 1 g of the polycarbonate diol of the formula (I) in the point of realizing an efficient reaction rate.

In the present invention, the reaction system is not particularly limited, and can be carried out in any systems including a batch system or a flow continuous system in which substrates are passing through a column of which an enzyme is immobilized.

(Scope of Solvent)

The reaction of the present invention can be carried out by using an organic solvent, or in the absence of a solvent. The organic solvent is not particularly limited so long as it can dissolve the substrate and does not deactivate the hydrolase.

The organic solvents may be mentioned at least one selected from, for example, aliphatic hydrocarbons such as n-pentane, n-hexane, n-heptane, n-octane, cyclopentane, cyclohexane and cycloheptane; aromatic hydrocarbons such as benzene, toluene and xylene; ethers such as diethyl ether, t-butyl methyl ether, diisopropyl ether, cyclopentyl methyl ether, tetrahydrofuran and 1,4-dioxane; ketones such as acetone and methyl ethyl ketone; nitriles such as acetonitrile and propionitrile, preferably n-hexane, n-heptane, cyclopentane, cyclohexane, toluene, diisopropyl ether, t-butyl methyl ether, cyclopentyl methyl ether or tetrahydrofuran, more preferably n-hexane, cyclohexane, toluene, diisopropyl ether, t-butyl methyl ether, cyclopentyl methyl ether and acetonitrile, particularly preferably cyclohexane, toluene and t-butyl methyl ether. These organic solvents may be used alone, or two or more in combination.

An amount of the organic solvent is preferably 0.1 to 100 mL, more preferably 0.5 to 50 mL, particularly preferably 1 to 10 mL based on 1 g of the polycarbonate diol of the formula (I).

The reaction of the present invention is preferably carried out in the co-presence of a polymerization inhibitor to prevent from polymerization of the acrylate portions. The polymerization inhibitor is not particularly limited so long as it is usually used, and may be used, for example, phenol, cresol, hydroquinone, t-butyl-hydroquinone, p-methoxyphenol (methoquinone), 2,6-di-t-butyl-4-methylphenol, phenothiazine, etc. An amount of the polymerization inhibitor is preferably 0.000001 to 0.05 mol, further preferably 0.000002 to 0.03 mol based on 1 mol of the polycarbonate diol.

(Scopes of the Reaction Temperature and Pressure)

In the present invention, the reaction temperature can be made 0 to 100° C., preferably 10 to 90° C., more preferably 40 to 80° C.

In the present invention, the reaction pressure is not particularly limited, and the reaction can be carried out under either of the conditions of a normal pressure or a reduced pressure.

Also, the reaction of the present invention may be carried out by a flow continuous system. When the reaction is carried out by the flow continuous system, a concentration of the polycarbonate diol compound in the reaction mixture is preferably set to 10 to 50% by mass based on the total mass of the reaction system, and a concentration of the vinyl acrylate compound is preferably 5 to 30% by mass based on the total mass of the reaction system. A linear velocity of the reaction mixture is preferably 0.5 to 400 mm/min, more preferably 1 to 200 mm/min. The linear velocity (mm/min) means a value represented by the quotient obtained by dividing a liquid feeding amount per 1 minute ($mm^3$/min) (or also called as a liquid feeding rate ($10^{-3}$ mL/min)) by a cross-sectional area ($mm^2$) of a packed bed. Liquid flow becomes difficult accompanying with increase in the pressure of the packed column by raising the linear velocity, whereby an oxygen packed column having high pressure resistance is required, and there is a fear that the immobilized enzyme is crushed due to increase of the pressure in the column. Thus, the linear velocity is preferably set to 400 mm/min or less. Also, the linear velocity is preferably set to 1 mm/min or more in the point of productivity. Expression activity of the immobilized enzyme changes based on the linear velocity, so that a reaction in accordance with a desired production ability and manufacturing costs can be carried out by selecting an optimum linear velocity and determining the reaction conditions. A residence time of the reaction mixture in the reactor can be made within the range of 30 seconds to 6 hours.

(High-Purity Polycarbonate Diol Dicarbonate)

The present invention also relates to a polycarbonate diol diacrylate represented by the formula (III):

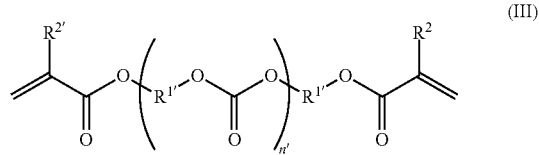

(III)

wherein $R^{1'}$ is the same or different, each represents a divalent group comprising one or more linear, branched or cyclic alkylene group, the divalent group may have a substituent(s), and/or one or more non-terminal carbon atoms may be replaced by a divalent aromatic group, a divalent heterocyclic group, an oxygen atom or a sulfur atom, or represents a divalent cross-linked carbon ring group, $R^{2'}$ represents a hydrogen atom or a linear or branched alkyl group having 1 to 4 carbon atoms, n' represents an average polymerization degree, and a number of 1 to 50, having a terminal acrylated ratio of 97% or more.

The terminal acrylated ratio means a ratio of the acrylate group occupied in the terminal group of the polycarbonate diol diacrylate represented by the formula (III).

The terminal acrylated ratio could be lowered due to the presence of the starting polycarbonate diol, or reaction by-products such as a monoacrylated product, etc. Also, in the process of reacting the polycarbonate diol and the acrylic acid ester compound in the presence of an organometallic catalyst while removing the forming alcohol, it is necessary to remove the alcohol to heighten the terminal acrylated ratio. However, the boiling points of the alcohol and the acrylic acid ester are generally close to each other, so that it is difficult to remove the alcohol alone. Moreover, due to the presence of the organometallic catalyst, the alcohol is exchanged to the carbonate bond of the polycarbonate diol to form a methoxy terminal. Both of these act to lower the terminal acrylated ratio.

By using the preparation process of the present invention, the polycarbonate diol diacrylate of the formula (III) having the terminal acrylated ratio of 97% or more can be easily obtained. The terminal acrylated ratio is preferably 98% or more.

Of these, a polycarbonate diol diacrylate also having a terminal alkoxylated ratio of less than 0.1% in the polycarbonate diol diacrylate of the formula (III) is preferred. As the alkoxy terminal, a methoxy terminal can be considered.

The terminal acrylated ratio and the terminal alkoxylated ratio can be measured by $^1$H-NMR analysis.

By using the preparation process of the present invention, terminal hydroxyl group derived from the starting polycarbonate diol can be reduced, and the polycarbonate diol diacrylate of the formula (III) in which a terminal hydroxyl group ratio obtained by subtracting the terminal acrylated ratio and the terminal alkoxylated ratio from 100% of less than 2% can be easily obtained.

When $R^{1'}$ is the divalent group comprising one or more linear, branched or cyclic alkylene group, there may be mentioned, for example, a divalent group comprising a linear or branched alkylene group-cyclic alkylene group, a divalent group comprising a linear or branched alkylene group-cyclic alkylene group-linear or branched alkylene group, and a divalent group comprising a cyclic alkylene group-linear or branched alkylene group-cyclic alkylene group.

A carbon number of the linear or branched alkylene group is preferably 1 to 25, more preferably 3 to 12, and there may be mentioned, for example, a propylene group, a butylene group, a pentylene group, a hexylene group, a 3-methylpentylene group, a heptylene group, an octylene group, a decylene group, etc., preferably a butylene group, a pentylene group, a hexylene group and a 3-methylpentylene group.

A number of the carbon atoms of the cyclic alkylene group is preferably 3 to 25, more preferably 3 to 12. The cyclic alkylene group is preferably a cycloalkylene having 3 to 12 carbon atoms, and may be mentioned, for example, a cyclopropylene group, a cyclobutylene group, a cyclopentylene group, a cyclohexylene group, a cycloheptylene group, a cyclooctylene group, etc., preferably a cyclohexylene group.

The above-mentioned divalent group comprising a linear or branched alkylene group-cyclic alkylene group-linear or branched alkylene group may be mentioned, for example, a cyclopentane-1,3-dimethylene group, a cyclohexane-1,4-dimethylene group, etc., preferably a cyclohexane-1,4-dimethylene group.

The above-mentioned divalent group may have a substituent(s) (for example, a benzene-1,4-dimethylene group), and/ or one or more carbon atoms other than the terminals of the divalent group (when the divalent group has a substituent(s), the portion other than the substituent(s)) may be replaced by a divalent aromatic group (for example, a phenylene group, a naphthylene group), a divalent heterocyclic group (for example, a pyridanyl group), an oxygen atom or a sulfur atom.

The substituent(s) may be mentioned a linear or branched alkyl group having 1 to 6 carbon atoms (for example, a methyl group, an ethyl group), a cycloalkyl group having 3 to 12 carbon atoms (for example, a cyclohexyl group), an aralkyl group having 7 to 10 carbon atoms (for example, a benzyl group), an aryl group having 6 to 12 carbon atoms (for example, a phenyl group, a tolyl group), an alkoxy group having 1 to 6 carbon atoms (for example, a methoxy group, an ethoxy group) and a halogen atom (for example, a fluorine atom, a chlorine atom).

$R^{1'}$ may be a divalent group of a cross-linked carbon ring. Here, "the cross-linked carbon ring" means a carbon ring in which two carbon atoms which are not adjacent to each other are cross-linked by a cross-linking group or a direct bond. The divalent group of the cross-linked carbon ring is preferably a divalent group of a cross-linked carbon ring having 6 to 10 carbon atoms, and there may be mentioned, for example, bicyclo-[2.1.1]-hexane-diyl, bicyclo-[2.2.1]-heptane-diyl, bicyclo-[2.2.2]-octane-diyl, bicyclo-[3.3.0]-octane-diyl, bicyclo-[4.3.0]-nonane-diyl, bicyclo-[4.4.0]-decane-diyl and adamantane-diyl.

$R^{1'}$ is preferably one or more selected from a propylene group, a butylene group, a pentylene group, a hexylene group, a 3-methylpentylene group, a cyclohexane-1,4-dimethylene group and a benzene-1,4-dimethylene group.

In the formula (III), n represents an average polymerization degree, and a number of 1 to 50, preferably 2 to 25. The average polymerization degree can be measured by terminal group determination using $^1$H-NMR.

When $R^{2'}$ is a linear or branched alkyl group having 1 to 4 carbon atoms, there may be mentioned, for example, a methyl group and an ethyl group. $R^{2'}$ is preferably a hydrogen atom or a methyl group.

The polycarbonate diol diacrylate of the present invention can be combined with a photopolymerization initiator to prepare a resin composition containing these components. Such a resin composition can be coated on a substrate, etc., and then, UV-ray is irradiated thereto by using a high-pressure mercury lamp, etc., to photocure the same. Also, it is combined with a radical initiator such as an organic peroxide, etc., and used as a resin composition containing these components. Such a resin composition can be coated on a substrate, etc., and then, cured by heating. The polycarbonate diol diacrylate of the present invention can be used as a starting material for ink, a paint, a coating material, an adhesive, a photocurable resin, a cross-linking agent, an electrolyte material, and other resins, etc.

EXAMPLES

Next, the present invention will be explained in more detail by referring to Examples, but the scope of the present invention is not limited by these.

An average molecular weight of the polycarbonate diol and the polycarbonate diol diacrylate was calculated from $^1$H-NMR measurement. From the average molecular weight, a polymerization degree was calculated. Also, a ratio in which the terminal hydroxyl group of the polycarbonate diol had been acrylated was calculated by $^1$H-NMR measurement.

Example 1

Acrylation of Polycarbonate Diol

To 1.0 g (0.5 mmol) of the polycarbonate diol (UI-1200 available from UBE INDUSTRIES, LTD., (poly(hexamethylenecarbonate))diol: average molecular weight 2000 (polymerization degree 14.6)) were added 5 mmol of vinyl acrylate and 1 mg of p-methoxyphenol as a polymerization inhibitor, and toluene was added to the mixture to a predetermined volume of 10 ml to prepare a reaction solution.

In a glass test tube were charged 2 ml of the above-mentioned reaction solution and 20 mg of the lipase (Novozym 435 (available from Novozymes) in which a lipase originated from *Candida antarctica* is immobilized to a resin porous material), and the mixture was reacted under stirring (1000 rpm) at 70° C. for 24 hours.

After completion of the reaction, the reaction mixture was filtered through a filter having a pore size of 0.2 μm, and the solvent in the filtrate was distilled off by using a rotary evaporator under reduced pressure. The residue was dried in a desiccator at 60° C. for 2 hours under reduced pressure to obtain a polycarbonate diol diacrylate, which was applied to $^1$H-NMR analysis.

A polycarbonate diol diacrylate was obtained in the same manner as mentioned above except for changing the reaction time to 48 hours, which was applied to $^1$H-NMR analysis.

The analytical results are shown in Table 1.

In the same manner as in Example 1 except for using the acrylates and the hydrolase shown in Table 1, polycarbonate diol diacrylates of Examples 2 to 4 and Comparative example 1 were prepared and applied to $^1$H-NMR analyses. The analytical results are shown in Table 1. Amano PS-CI (available from Amano Enzyme Co.) is an immobilized catalyst in which a lipase originated from *Burkholderia cepacia* is adsorbed to a porous ceramic carrier.

TABLE 1

|  | Acrylic acid ester | Hydrolase | Reaction time (h) | Polymerization degree (n) | Terminal acrylated ratio (%) | Methoxy terminal (%) |
|---|---|---|---|---|---|---|
| Example 1 | Vinyl acrylate | Novozym 435 | 24 | 14.2 | 95.7 | n.d. |
|  |  |  | 48 | 13.9 | >99 | n.d. |
| Example 2 | Vinyl acrylate | Amano PS-CI | 24 | 13.7 | 64.8 | n.d. |
|  |  |  | 48 | 14.1 | 78.7 | n.d. |
| Example 3 | Vinyl methacrylate | Novozym 435 | 24 | 12.5 | 98.5 | n.d. |
|  |  |  | 48 | 12.6 | >99 | n.d. |
| Example 4 | Vinyl methacrylate | Amano PS-CI | 24 | 13.6 | 85.5 | n.d. |
|  |  |  | 48 | 13.5 | 91.4 | n.d. |

TABLE 1-continued

|  | Acrylic acid ester | Hydrolase | Reaction time (h) | Polymerization degree (n) | Terminal acrylated ratio (%) | Methoxy terminal (%) |
|---|---|---|---|---|---|---|
| Comparative example 1 | Methyl acrylate | Novozym 435 | 24<br>48 | 4.1<br>3.5 | 68.8<br>68.1 | 27.1<br>27.8 |

When methyl acrylate was used as the acrylic acid ester and Novozym 435 was used as a hydrolase, remarkable lowering in the polymerization degree and a methoxy terminal in which the by-produced alcohol was exchanged with the main chain carbonate were found (Comparative example 1). When methyl acrylate was used as the acrylic acid ester and Amano PS-CI was used as a hydrolase, the terminal acrylated ratio was remained to a low value (Comparative example 2).

On the other hand, when vinyl acrylate or vinyl methacrylate was used as the acrylic acid ester and Novozym 435 or Amano PS-CI was used as a hydrolase, polycarbonate diol diacrylates having high terminal acrylated ratios without lowering polymerization degree can be obtained (Examples 1 to 4). In particular, the terminal acrylated ratios of Examples 1 and 3 using Novozym 435 were extremely high, and the terminal hydroxyl group ratio after 48 hours was less than 1%.

Examples 5 to 7 Acrylation of Polycarbonate Diol

To 3.0 g of the polycarbonate diol shown in Table 2 were added 2 equivalents (each 1.35 g in Example 5 (UH100) and Example 6 (U C 100), and 1.51 g in Example 7 (UM90 (1/1): a polycarbonate diol comprising a 1,6-hexanediol residue and a 1,4-cyclohexanedimethanol residue in an equivalent molar)) of vinyl methacrylate to the terminal hydroxyl group, and 1 mg of p-methoxyphenol as a polymerization inhibitor, and toluene was added to the mixture to a predetermined volume of 10 ml to prepare a reaction solution.

In a glass test tube were charged 2 ml of the above-mentioned reaction solution and 5 mg of the lipase (Novozym 435), and the mixture was reacted under stirring (1000 rpm) at 70° C. for the time shown in Table 2.

After completion of the reaction, each of the reaction mixture was filtered through a filter of 0.2 μm, and the solvent in each of the filtrate was distilled off by using a rotary evaporator under reduced pressure. The residue was dried in a desiccator at 60° C. for 2 hours under reduced pressure to obtain each of a polycarbonate diol diacrylate, which was applied to $^1$H-NMR analysis. The results are shown in Table 3.

TABLE 2

|  | Polycarbonate diol (PCD) | Composition | Average molecular weight | Polymerization degree (n) |
|---|---|---|---|---|
| Example 5 | UH100 (available from UBE INDUSTRIES, LTD.) | Poly(1,6-hexanediol carbonate) diol | 1000 | 7.0 |
| Example 6 | UC100 (available from UBE INDUSTRIES, LTD.) | Poly(1,4-cyclohexane-dimethanol carbonate) diol | 1000 | 5.7 |
| Example 7 | UM90 (1/1) (available from UBE INDUSTRIES, LTD.) | 1,6-Hexanediol/1,4-cyclohexanedimethanol copolymerized carbonate diol (molar ratio = 1:1) | 900 | 6.0 |

TABLE 3

|  | Polycarbonate diol (PCD) | Reaction time (h) | Polymerization degree (n) | Terminal acrylated ratio (%) | Methoxy terminal (%) |
|---|---|---|---|---|---|
| Example 5 | UH100 (available from UBE INDUSTRIES, LTD.) | 3<br>24 | 7.1<br>7.0 | 74.4<br>>99 | n.d.<br>n.d. |
| Example 6 | UC100 (available from UBE INDUSTRIES, LTD.) | 3<br>24 | 5.6<br>6.0 | 80.3<br>>99 | n.d.<br>n.d. |
| Example 7 | UM90 (1/1) (available from UBE INDUSTRIES, LTD.) | 3<br>24 | 5.9<br>6.0 | 96.2<br>>99 | n.d.<br>n.d. |

In either of Examples 5 to 7, a polycarbonate diol diacrylate was obtained with a high terminal acrylated ratio. Also, the terminal hydroxyl group ratio after 24 hours was less than 1%.

Examples 8 to 10

Acrylation of Polycarbonate Diol by Continuous Reaction Using Immobilized Enzyme To 150 g of the polycarbonate diol (UH100, see Table 2) were added 67.5 g of vinyl methacrylate and 0.05 g of p-methoxyphenol as a polymerization inhibitor, and toluene was added to the mixture to a predetermined volume of 500 ml to prepare a reaction solution.

In a glass column (inner diameter 5 mm×50 mm, with a glass filter having a pore size of 5 μm) was packed 0.42 g of the immobilized lipase (Novozym 435), the mixture was maintained at 70° C., and the reaction solution was fed from the bottom with a flow rate shown in Table 4 using a quantitative pump.

The reaction mixture was fractionated with each time shown in Table 4, and with regard to the obtained reaction mixture, the solvent was distilled off by a rotary evaporator under reduced pressure. The residue was dried in a desiccator at 60° C. for 2 hours under reduced pressure, which was applied to $^1$H-NMR analysis.

TABLE 4

| Example | Flowing rate | Residence time (h) | Terminal acrylated ratio (%) |
|---|---|---|---|
| 8 | 0.037 ml/min | 1 | >99 |
|  |  | 2 | >99 |
|  |  | 3 | >99 |
|  |  | 6 | >99 |
| 9 | 0.11 ml/min | 1 | 93.9 |
|  |  | 2 | 92.1 |
|  |  | 3 | 90.5 |
|  |  | 6 | 87.3 |
| 10 | 0.30 ml/min | 1 | 65.1 |
|  |  | 2 | 63.7 |
|  |  | 3 | 60.2 |
|  |  | 6 | 57.4 |

In either of Examples 8 to 10, a polycarbonate diol diacrylate was obtained with a high terminal acrylated ratio. In particular, the terminal hydroxyl group ratios of Example 8 were all less than 1% in either of the residence times.

UTILIZABILITY IN INDUSTRY

According to the present invention, the polycarbonate diol diacrylate can be prepared from a polycarbonate diol and a vinyl acrylate compound by using a hydrolase without using a protonic acid or a metal component. The process of the present invention can be carried out at a relatively low temperature so that it is excellent in the points of efficiency and safety. Moreover, according to the process of the present invention, a high quality polycarbonate diol diacrylate with a high terminal acrylated ratio can be obtained. That is, according to the present invention, a high quality polycarbonate diol diacrylate can be easily prepared by using easily available starting materials.

The invention claimed is:

1. A process for preparing a polycarbonate diol diacrylate which comprises reacting a polycarbonate diol represented by the formula (I):

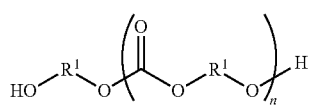

wherein
$R^1$ is the same or different, each represents a divalent group comprising one or more linear, branched or cyclic alkylene group, the divalent group may have a substituent(s), and/or one or more non-terminal carbon atoms may be replaced by a divalent aromatic group, a divalent heterocyclic group, an oxygen atom or a sulfur atom, or represents a divalent cross-linked carbon ring group,
n represents an average polymerization degree, and a number of 1 to 50,
with a vinyl acrylate compound represented by the formula (II):

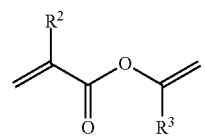

wherein
$R^2$ represents a hydrogen atom or a linear or branched alkyl group having 1 to 4 carbon atoms,
$R^3$ represents a hydrogen atom or a linear, branched or cyclic alkyl group having 1 to 10 carbon atoms in the presence of a hydrolase.

2. The process for preparing a polycarbonate diol diacrylate according to claim 1, wherein the hydrolase is a lipase.

3. The process for preparing a polycarbonate diol diacrylate according to claim 2, wherein the lipase is an immobilized lipase.

4. The process for preparing a polycarbonate diol diacrylate according to claim 3, wherein the reaction is carried out in a flow tube reactor filled with the immobilized lipase.

5. The process for preparing a polycarbonate diol diacrylate according to claim 2, wherein the lipase is a lipase originating from *Candida antarctica*.

6. A polycarbonate diol diacrylate represented by the formula (III):

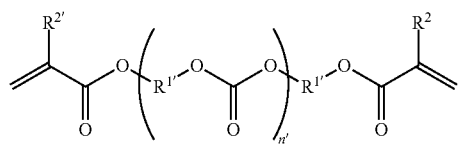

wherein
$R^{1'}$ is the same or different, each represents a divalent group comprising one or more linear, branched or cyclic alkylene group, the divalent group may have a substituent(s), and/or one or more non-terminal carbon atoms may be replaced by a divalent aromatic group, a divalent heterocyclic group, an oxygen atom or a sulfur atom, or represents a divalent cross-linked carbon ring group,
$R^{2'}$ represents a hydrogen atom or a linear or branched alkyl group having 1 to 4 carbon atoms, n' represents an average polymerization degree, and a number of 1 to 50,
having a terminal acrylated ratio of 97% or more.

7. The polycarbonate diol diacrylate according to claim 6, wherein a terminal alkoxylated ratio is less than 0.1%.

8. The polycarbonate diol diacrylate according to claim 6, wherein a terminal hydroxyl group ratio is less than 1%.

9. The process for preparing a polycarbonate diol diacrylate according to claim 3, wherein the lipase is a lipase originating from *Candida antarctica*.

10. The process for preparing a polycarbonate diol diacrylate according to claim 4, wherein the lipase is a lipase originating from *Candida antarctica*.

11. The polycarbonate diol diacrylate according to claim 7, wherein a terminal hydroxyl group ratio is less than 1%.

* * * * *